United States Patent [19]
Attermeier

[11] Patent Number: 4,662,599
[45] Date of Patent: May 5, 1987

[54] ROLLER CLAMP HAVING IMPROVED INFEED SECTION

[75] Inventor: Kurt R. Attermeier, Round Lake Park, Ill.

[73] Assignee: Baxter Travenol Laboratories, Inc., Deerfield, Ill.

[21] Appl. No.: 904,740

[22] Filed: Sep. 5, 1986

[51] Int. Cl.⁴ .............................................. F16L 55/14
[52] U.S. Cl. ........................................... 251/6; 251/4
[58] Field of Search ....................... 251/4, 6; 604/250

[56] References Cited

U.S. PATENT DOCUMENTS

| Re. 31,584 | 5/1984 | Adelberg | 251/6 |
| 1,959,074 | 5/1934 | Bloxsom | 251/6 |
| 3,099,429 | 7/1963 | Broman | 251/4 |
| 3,189,038 | 6/1965 | Von Pechmann | 251/6 |
| 4,238,108 | 12/1980 | Muetterties | 251/6 |
| 4,553,963 | 11/1985 | Young | 251/6 |

Primary Examiner—Martin P. Schwadron
Assistant Examiner—Sheri M. Novack
Attorney, Agent, or Firm—Paul C. Flattery; Kay H. Pierce

[57] ABSTRACT

A novel roller clamp is described for controlling flow of fluids in flexible tubing used for intravenous fluid administration to a patient. The roller clamp includes a unique placement means to enhance placement of a roller within a clamp body or frame. The novel placement means includes angular portions disposed in an infeed section of the frame. The angular portions form an angle greater than 90 degrees with a side wall portion of the frame to encourage upward movement of the roller during insertion onto guide surfaces in the frame of the clamp.

8 Claims, 6 Drawing Figures

4,662,599

ROLLER CLAMP HAVING IMPROVED INFEED SECTION

BACKGROUND OF THE INVENTION

This invention relates to an improved flow control unit for accurately controlling the flow of fluid through a length of flexible I.V. tubing. More particularly, this invention relates to a disposable clamp and flow control member utilizing a roller member to exert a controlled force on a length of tubing.

Roller clamp devices are commonly used to control flow of fluids through flexible tubing during intravenous administration of fluids to patients. For example, various roller clamp devices are described in U.S. Pat. Nos. 3,189,038 entitled "Variable Flow Clamp for Flexible Tubing"; RE. 31,584 entitled "Apparatus for Regulating Fluid Flow Through Plastic Tubing"; and 4,238,108 entitled "Flow Control Device". U.S. Pat. No. 4,238,108 is of particular interest because it describes a novel structure for inserting a roller into a clamp body. Once the roller is placed in the clamp body, it is difficult to remove without excessive force.

One advantage of the invention described herein over the prior art is that during assembly of a roller clamp designed in accordance with the invention, ease of insertion of a roller into the clamp body is greatly enhanced.

Another advantage of the present invention is that minimal stress to the clamping body is produced due to insertion of the roller.

SUMMARY OF THE INVENTION

The invention can be described as a disposable roller-type tubing clamp for regulating flow of fluid through a length of flexible tubing. The invention includes a clamp body defining a rigid support surface for the length of flexible tubing. The clamp body has a longitudinal axis. The clamp body also has first and second ends. The clamp body also includes opposing semiflexible walls extending from the support surface which define opposing track members with guide surfaces integrally disposed in the walls. The guide surfaces are spaced from the support surface a predetermined distance and extend substantially in a direction of the longitudinal axis. The opposing walls are spaced from each other and define an open slot therebetween. The clamp body still further includes an open infeed section in the first end of the clamp body which extends between the walls. The infeed section includes a floor portion spaced from an end of the support surface. The floor portion is spaced from the guide surfaces a distance greater than the said support surface, and the guide surfaces extend into at least a portion of the infeed section. The roller clamp also includes a rotatable member having trunnions positioned to be captively guided and rotated along the guide surfaces with the track members providing confining wall surfaces for the ends of the trunnions. The clamping body also includes a unique rotatable member placement means for enhancing placement of the rotatable member onto the guide surfaces, the placement means including angular portions disposed in the infeed section generally extending in a continuous manner inwardly from each of the guide surfaces to the opposing wall at a location intermediate the floor portion and the guide surface, each angular portion having an angle with respect to the side wall of greater than 90 degrees for the purpose of urging the trunnions of the rotatable member upwardly onto the guide surfaces when the rotatable member is in contact with the angular portion in the infeed section.

DETAILED DESCRIPTION OF THE PREFERRED EMBODIMENT

Figure 1:
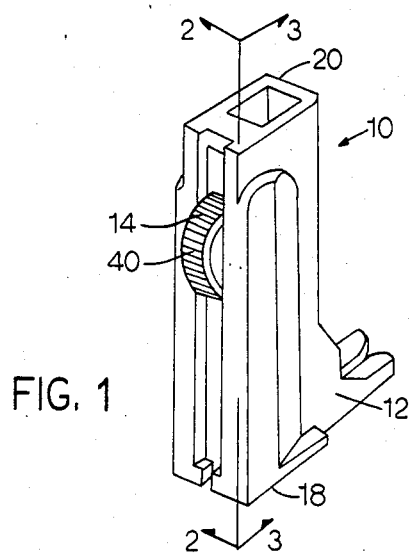
FIG. 1 is a perspective view of a roller clamp in accordance with the subject invention.

Referring now to FIG. 1, a roller clamp designated generally 10 includes a clamping body 12, and a rotatable member or roller 14. The clamping body 12 defines a rigid support surface 16, FIG. 4, for supporting a length of flexible tubing. The clamping body includes a first end 18, and a second end 20.

Opposing semiflexible walls 22 extend from the support surface 16, and define opposing track members 24 with guide surfaces 28 integrally disposed in the walls. The guide surfaces are spaced from the support surface 16 a predetermined distance and extend substantially in a direction parallel with the longitudinal axis of the roller clamp 10. The opposing walls 22 are spaced apart from each other and are generally parallel to create an open slot therebetween.

Figure 2:
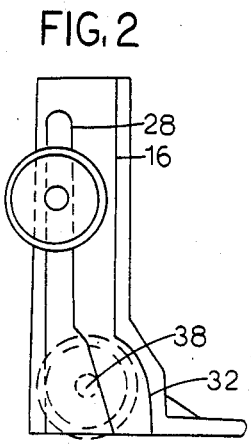
FIG. 2 is a view in horizontal section taken along the line 2—2 in FIG. 1.

The clamping body 12 includes an open infeed section 30 at the first end 18 of the clamping body 12. The infeed section 30 includes a floor portion 32 spaced from an end 34 of the support surface 16. As can be seen in FIG. 2, the floor portion 32 is spaced from the guide surfaces 28 a distance greater than the distance between the support surface 16 and the guide surface 28. In the preferred embodiment, the guide surfaces 28 extend into at least a portion of the infeed section 30 as illustrated by element 36 in FIG. 4.

The roller clamp includes a roller or rotatable member 14 having trunnions 38 which extend axially outward from a clamping surface 40 on the roller 14. The trunnions are designed to extend outwardly a sufficient distance to allow the trunnions to be captively guided and rotated along the guide surfaces 28 of track members 24. More particularly, the length of the roller from trunnion to trunnion is generally greater than the distance between the opposing wall portions below the guide surfaces 28 of the track members.

The roller clamp described herein includes a novel rotatable member placement means 42 for enhancing placement of the rotatable member 14 onto the guide surfaces during assembly of the roller clamp. The placement means includes angular portions 44, FIG. 4, disposed in the infeed section 30 of the clamping body 12. The angular wall portions extend generally inwardly in a continuous manner from each of the guide surfaces 28 to its associated opposing wall 46 at a location intermediate the floor portion 32 and the guide surface 28. Each angular portion has an angle with respect to its associated opposing wall 46 of greater than 90 degrees. This angle urges the trunnions 38 of the rotatable member 14 upwardly onto the guide surfaces 28 when the trunnions of the rotatable member 14 are in contact with the angular portion 44 of the infeed section 30.

The invention described is advantageous over the prior art because the angular portions continuously urge the trunnions up onto the guide surfaces of the clamping body while reducing the force necessary to insert the roller and, therefore, reducing the stress on the clamping body during insertion. By requiring that the angular portions have a greater than 90 degree angle relative to its associated opposing wall surface, rather than a 90 degree angle ridge as taught in the prior art, the trunnions of the roller are urged immediately upward onto the guide surfaces during assembly. This allows the trunnions of the roller to cause minimal spreading, and thus stress, of the opposing walls of the clamping body during assembly of the roller into the clamping body because the trunnions tend to engage the guides surfaces 28 close to the first end 18 of the clamping body.

Figure 4:
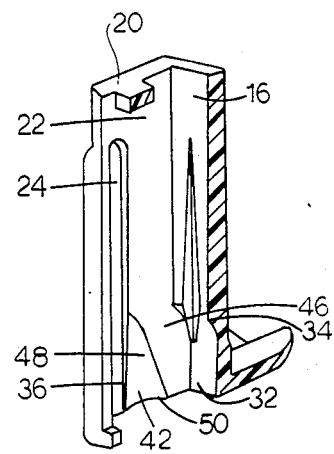
FIG. 4 is a perspective view of section 2—2 in FIG. 1.
Figure 5:
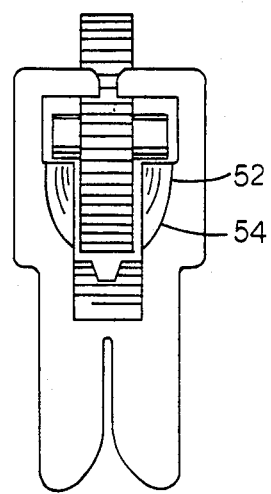
FIG. 5 is an end view of the preferred embodiment of the invention.

The angular portions are generally in the form of a triangular surface 48 having its widest portion 50 at the first end of the clamping body, FIG. 4. In the preferred embodiment of the subject invention as illustrated in FIG. 5, each surface 48 has a generally flat portion 52 extending downwardly from guide surface 28. The flat portion in the preferred embodiment is substantially parallel to the opposing wall 22. In the preferred embodiment, each surface also includes a curved portion 54, which extends from the flat portion 52 to its associated opposing wall. In one embodiment of the invention, the curved portion 54 may have a radius ranging from 0.050 to 0.0170 inches. At the first end of the clamp body, approximately 40% of the angular portion is curved. The ratio of curved to flat portions gradually increases toward the second end of the clamp body. At the end of the angular portion closest to the second end of the clamp body, the angular portion does not contain a flat portion. In other embodiments of the invention the percentage of the curved portion may range from 25% to 60%.

Figure 6:
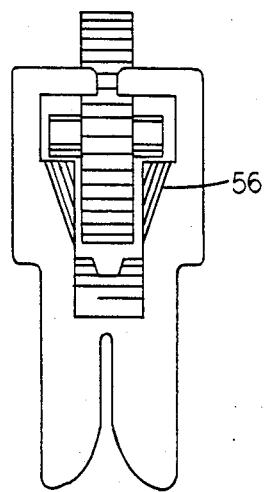
FIG. 6 is an end view of an alternative embodiment of the invention.

In another embodiment of the invention, each surface of the angular portion is totally flat. This is illustrated by element 56, FIG. 6. In both the embodiments illustrated in FIGS. 5 and 6, the angle formed by the juncture of the surface with its associated opposing wall may range from 105 to 175 degrees in various embodiments. In a preferred embodiment of the invention, this angle may range from 150 to 170 degrees, and in a particularly preferred embodiment, the angle is on the order of 160 degrees.

Figure 3:
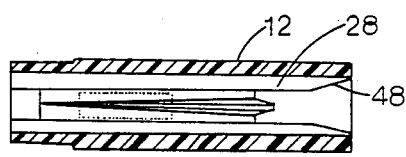
FIG. 3 is a view in vertical section taken along the line 3—3 in FIG. 1.

Referring now to FIG. 3, the guide surface 28 tapers at an angle at the first end of the clamping body in the infeed section. The angle may range from 5 to 10 degrees with respect to the longitudinal axis of the clamp body. In the preferred embodiment, the angle is 7 degrees. Since the tapered portion of the guide surface is connected to the angular portion, the angular portion also forms a 7 degree angle with respect to the longitudinal axis in the preferred embodiment.

Although the invention has been described and illustrated in detail, it is to be clearly understood that the same is by way of illustration and example only, and is not to be taken by way of limitation; the spirit and scope of this invention being limited only by the terms of the appended claims.

That which is claimed:

1. A disposable roller-type tubing clamp for regulating flow of fluid through a length of flexible tubing comprising a portion of an intravenous administration set, the invention comprising:

a clamp body defining a rigid support surface for said length of flexible tubing, said clamp body having a longitudinal axis, said clamp body having first and second ends;

opposing semiflexible walls extending from said support surface defining opposing track members with guide surfaces integrally disposed in said walls, said guide surfaces spaced from said support surface a predetermined distance and extending substantially in a direction of said longitudinal axis, said opposing walls spaced from each other and generally parallel with each other to define an open slot therebetween;

an open infeed section in said first end of said clamp body, said infeed section including a floor portion spaced from an end of said support surface, said floor portion spaced from said guide surfaces a distance greater than said support surface, said guide surfaces extending in at least a portion of said infeed section;

a rotatable member having trunnions positioned to be captively guided and rotated along said guide surfaces with said track members providing confining wall surfaces for the ends of said trunnions; and rotatable member placement means for enhancing placement of said rotatable member onto said guide surfaces, said placement means including angular portions disposed in said infeed section generally extending in a continuous manner inwardly from each of said guide surfaces and joining said wall at a location intermediate said floor portion and said guide surface, each angular portion having an angle with respect to said wall of greater than 90 degrees to urge trunnions of said rotatable member upwardly onto said guide surfaces when said rotatable member is in contact with said angular portion in said infeed section.

2. A disposable roller-type tubing clamp as recited in claim 1 wherein:

each of said angular portions is generally in the form of a triangular surface having its widest portion at the end of the infeed section away from said section end.

3. A disposable roller-type tubing clamp as recited in claim 2 wherein:

each surface of said angular portions including a flat portion extending from said guide surface, said flat portion being substantially parallel to said wall, said surface also including a curved portion extending from said flat portion to said wall.

4. A disposable roller-type tubing clamp as recited in claim 2 wherein:

each surface of said angular portion is a flat surface.

5. A disposable roller-type tubing clamp as recited in claim 2 wherein:

said portion extends to said wall and forms and angle with said wall ranging from 105 to 175 degrees.

6. A disposable roller-type tubing clamp as recited in claim 2 wherein:

said portion extends to said opposing wall and forms an angle with said wall ranging from 150 to 175 degrees.

7. A disposable roller-type tubing clamp as recited in claim 2 wherein:

said portion extends to said opposing wall and forms an angle with said wall on the order of 160 degrees.

8. A disposable roller-type tubing clamp as recited in claim 3 wherein:

said curved portion has a radius ranging from 0.050 to 0.170 inches.

* * * * *